(12) United States Patent
Lan et al.

(10) Patent No.: US 10,165,994 B2
(45) Date of Patent: Jan. 1, 2019

(54) HANDHELD X-RAY DEVICE BY COLD CATHODE

(71) Applicant: Energy Resources International Co., Ltd., New Taipei (TW)

(72) Inventors: Wen-How Lan, New Taipei (TW); Yi-Teng Shiu, New Taipei (TW); Hung-Chiang Huang, New Taipei (TW); Reng-Sho Chen, New Taipei (TW); Shu-Fen Liao, New Taipei (TW); Yu-Wei Chen, New Taipei (TW)

(73) Assignee: Energy Resources International Co., Ltd., New Taipei (TW)

( * ) Notice: Subject to any disclaimer, the term of this patent is extended or adjusted under 35 U.S.C. 154(b) by 195 days.

(21) Appl. No.: 14/996,862

(22) Filed: Jan. 15, 2016

(65) Prior Publication Data

US 2016/0206261 A1 Jul. 21, 2016

(30) Foreign Application Priority Data

Jan. 15, 2015 (TW) .............................. 104101437 A (51) Int. Cl.
*A61B 6/00* (2006.01)

(52) U.S. Cl.
CPC ................ *A61B 6/462* (2013.01); *A61B 6/40* (2013.01); *A61B 6/4405* (2013.01); *A61B 6/465* (2013.01); *A61B 6/542* (2013.01); *A61B 6/587* (2013.01); *H01J 2235/062* (2013.01)

(58) Field of Classification Search
CPC .. A61B 6/10; A61B 6/107; A61B 6/14; A61B 6/40; A61B 6/4405; A61B 6/462; A61B 6/465; A61B 6/542; H01J 35/065; H01J 35/16; H01J 35/02; H01J 2235/062; H01J 2235/16; H01J 2235/165; H05G 1/06; H05G 1/10; H05G 1/38
See application file for complete search history.

(56) References Cited

U.S. PATENT DOCUMENTS 2,214,871 A * 9/1940 Westendorp .......... H02M 7/103
   315/15
4,694,480 A * 9/1987 Skillicorn ............... H01J 35/12
   378/102

(Continued)

OTHER PUBLICATIONS

Translation of CN 103219212 published Jul. 24, 2013.*

*Primary Examiner* — Chih-Cheng Kao
(74) *Attorney, Agent, or Firm* — Muncy, Geissler, Olds & Lowe, P.C.

(57) ABSTRACT

A handheld X ray device comprises a camera-like X ray generator body having a zoom ring-like object at a front side of the X ray generator body as an exit of X rays and has a collimator section atop a surface of the zoom ring-like object. The camera-like X ray generator body inside has a voltage boosting circuit, an oscillator circuit, a battery, and a control circuit, and a user interface at a real panel of the camera-like X ray generator body. The glass ball-tube is a cold cathode type X-ray generator with a tungsten filament at a periphery of a cold cathode. The voltage boosting circuit, the oscillator circuit, boosting the voltage of the battery up to a predetermined high voltage under controlled of the control circuit assisting by the user interface.

3 Claims, 6 Drawing Sheets

(56) References Cited

U.S. PATENT DOCUMENTS

| | | | | |
|---|---|---|---|---|
| 6,320,936 | B1 * | 11/2001 | Holland, Sr. | G21K 1/02 |
| | | | | 378/140 |
| 6,553,096 | B1 | 4/2003 | Zhou et al. | |
| 6,614,873 | B1 * | 9/2003 | Taylor | A61B 6/4233 |
| | | | | 378/62 |
| D710,424 | S * | 8/2014 | Hallgren | D16/206 |
| 2005/0084068 | A1 * | 4/2005 | Matsuno | A61B 6/4225 |
| | | | | 378/96 |
| 2005/0129178 | A1 * | 6/2005 | Pettit | B82Y 10/00 |
| | | | | 378/122 |
| 2007/0269010 | A1 * | 11/2007 | Turner | A61B 6/4405 |
| | | | | 378/102 |
| 2014/0362972 | A1 * | 12/2014 | Ogura | H01J 35/14 |
| | | | | 378/62 |
| 2016/0021725 | A1 * | 1/2016 | Pellechia | G01N 23/04 |
| | | | | 378/198 |
| 2016/0079029 | A1 * | 3/2016 | Li | H01J 35/06 |
| | | | | 378/122 |

\* cited by examiner

HANDHELD X-RAY DEVICE BY COLD CATHODE

FIELD OF THE INVENTION

The present invention pertains to a cold cathode type handheld X ray device and with a friendly user interface.

DESCRIPTION OF THE PRIOR ART

An x-ray generation device with a cold cathode generating field emission electrons is known according to a quantum theory of field electron emission. The basic principle of the field emission electrons is that the electrons of a conductor must have sufficient energy to get a chance to cross the potential energy barrier to the vacuum side when no electric field is applied. When an electric field is applied the energy band is bent, as a result, electrons cross the potential energy barrier to the vacuum side without huge amount of energy. When the applied electric field is increasing, the potential energy barrier by electrons is decreasing and the strength of the derived current is increasing. According to electromagnetic theory, if a charged object has a sharp point, the electric field strength around that point will be much higher than elsewhere. Air near the electrode can become ionized (partially conductive), while regions more distant do not. Therefore, for a field emission cathode, more upperward carbon fibers are desired so that the electric field will be generated even the applied voltage on the cathode is low.

At present time, an x-ray generation device usually serves as an electron source within a microwave element, sensor, panel display, or the like. The efficiency of electron emission mostly depends on the element structure, material, and shape of a field emission cathode (i.e. an x-ray generation device). A field emission cathode is made of metal, such as silicon, diamond, and carbon nano-tube. Among these materials, carbon nano-tube is particularly important because its openings are extremely thin and stable, it has low conducted field and high emitting current density, and it is highly stable. With these characteristics, carbon nano-tube is extremely suitable for a field emission cathode. Therefore, it is highly possible that carbon nano-tube will replace other materials and becomes the material of field emission in the next generation.

Field emission cathode can serve as a cathode of an x-ray generation device, such as an x-ray tube. An x-ray generation device encapsulates a cathode, electromagnetic-lens aperture, and an anode target within a glass container. The conventional thermionic cathode neon tube can be replaced by the carbon nano-tube. When using a thermionic cathode neon tube in an x-ray generation device, around 99% of electricity is transformed to heat. Thus, the thermionic cathode neon tube must be cool down by cooling water. On the contrary, carbon nano-tube can emit electron beams under smaller electric field intensity, so the efficiency of transferring electricity to electronic beams is higher than that of thermionic cathode nano-tube. In addition, cooling process is not required when using a carbon nano-tube type x-ray device.

The U.S. Pat. No. 6,553,096 presented by Zhou et al. discloses an x-ray generation device adopting carbon nano-tubes. Zhou et al. use materials with nanometer structures as an emitting source of a cathode field emission. Furthermore, Zhou et al. claimed that a current density of about 30 mA/cm$^2$ generated can be achieved by an x-ray generator using carbon nano-tubes. The x-ray generator has a threshold electric field of about 3.5 V/μm. However, at that current density, the current is not stable.

Figure 4:
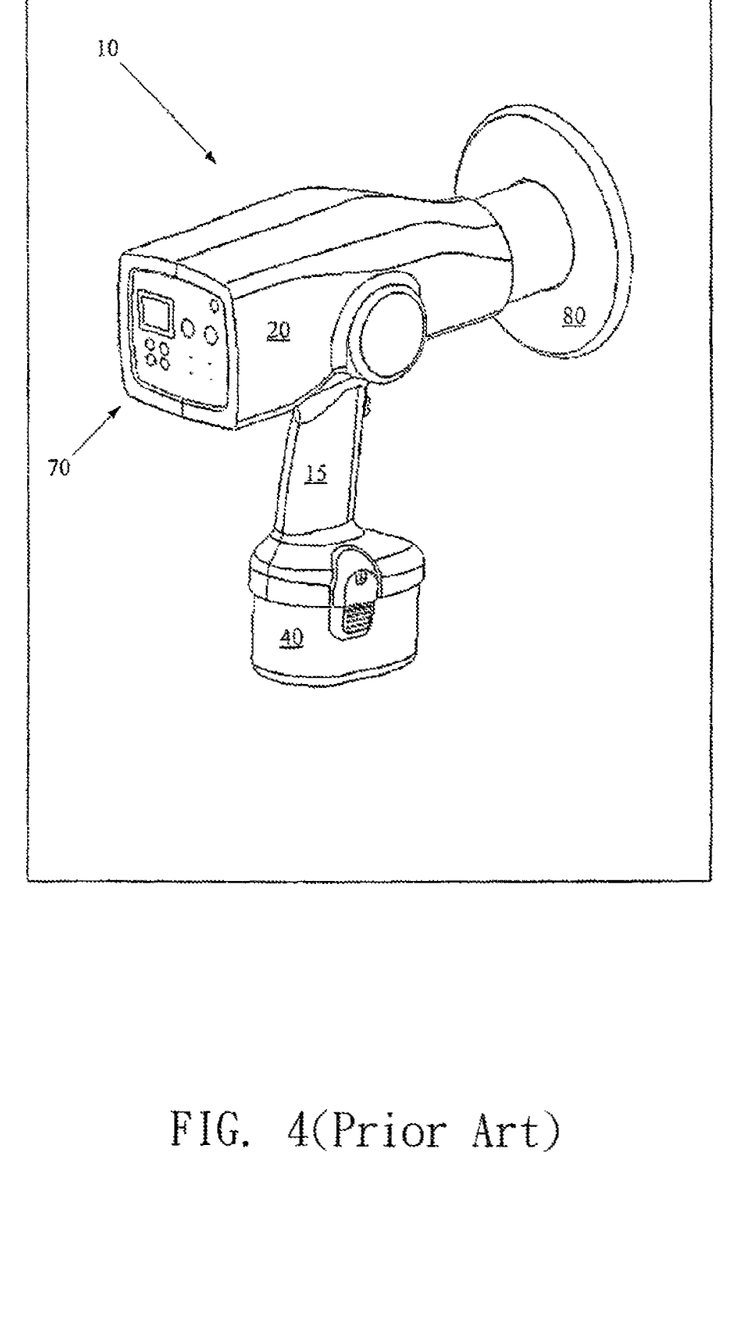
FIG. 4 illustrates a schematic diagram of a handheld X-ray in accordance with the prior art.

A well known handheld X ray device may be the Normad Pro 2 manufactured by ARIBEX Company. Please refer to U.S. Pat. No. 7,496,178 or refer to FIG. 4. The handheld X ray device has a hot-electron type cathode and a pistol like body 10. In the front end of the gun barrel there is a lead disk 80 to shield the irradiation. At the back plate of the hand gun 10 there is a LCD display 60. Under the handle grip, there is a battery 40 to provide electrical power for a voltage boosting module to generate a high voltage for X ray generator. The handheld X ray has to be interrupted at least 1 minute for cooling after each shot, thus, the X ray cannot emit X-ray continuously. The lead disk 80 may hinder the operator from accuracy alignment.

Thus, a present invention is to provide a technology to solve the foregoing problem.

SUMMARY OF THE INVENTION

An object of the present invention is to provide features of lightweight, low current, free cooling, and continuous X-ray emission.

The other object of the present invention is to provide a cold cathode type handheld X ray device and is capable of keeping a vacuum level in the glass ball tube as the initial even after the X-ray generator used for a long time so as to keep the X-ray photo quality well.

Another object of the present invention is to provide an operator could easily sight at predetermined site to carry out X ray irradiation.

The present invention discloses a handheld X ray device comprises a camera-like X ray generator body having a zoom ring-like object at a front side of the X ray generator body as an exit of X rays and has a collimator section atop a surface of the zoom ring-like object. The camera-like X ray generator body inside has an oscillator circuit, a battery, a control circuit, and a user interface. The glass ball-tube is a cold cathode type X-ray generator with a tungsten filament at a periphery of a cold cathode.

The glass ball-tube and the voltage boosting module are encapsulated by an insulating gel and wrapped by a lead shell except an X ray window, wherein the voltage boosting circuit is provided to output a predetermined high voltage to the anode electrode pin, which is extended out from a glass ball-tube, and the cathode is grounded. The voltage of the battery is boosted up by the voltage boosting circuit to a voltage of about 40 kV-70 kV under controlled by said control circuit. The user interface, connected to the control circuit provided to let an operator setting or changing default value according to the conditions of a patient, and the user interface includes a security button to prevent the handheld X ray device from being actuated unsafely.

DESCRIPTION OF THE PREFERRED EMBODIMENT

Figure 1:
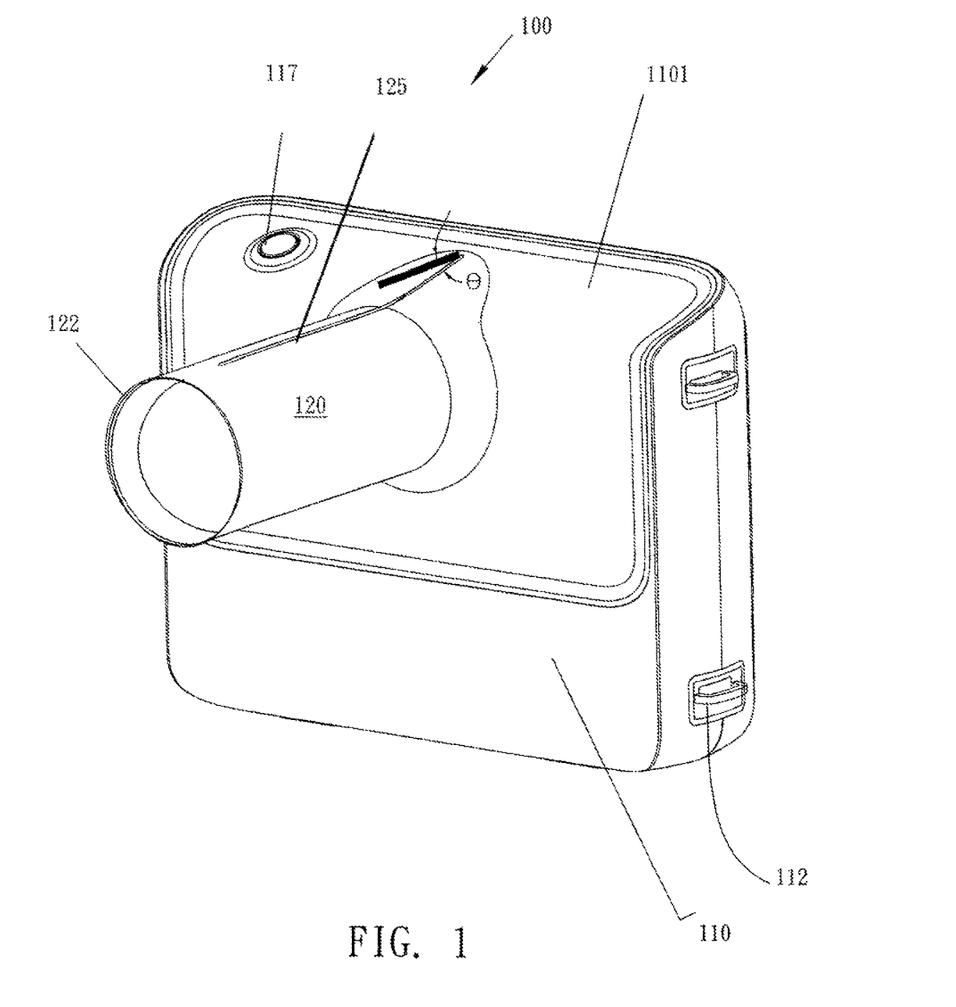
FIG. 1 is a perspective view of a handheld X ray device in accordance with the present invention.
Figure 2A:
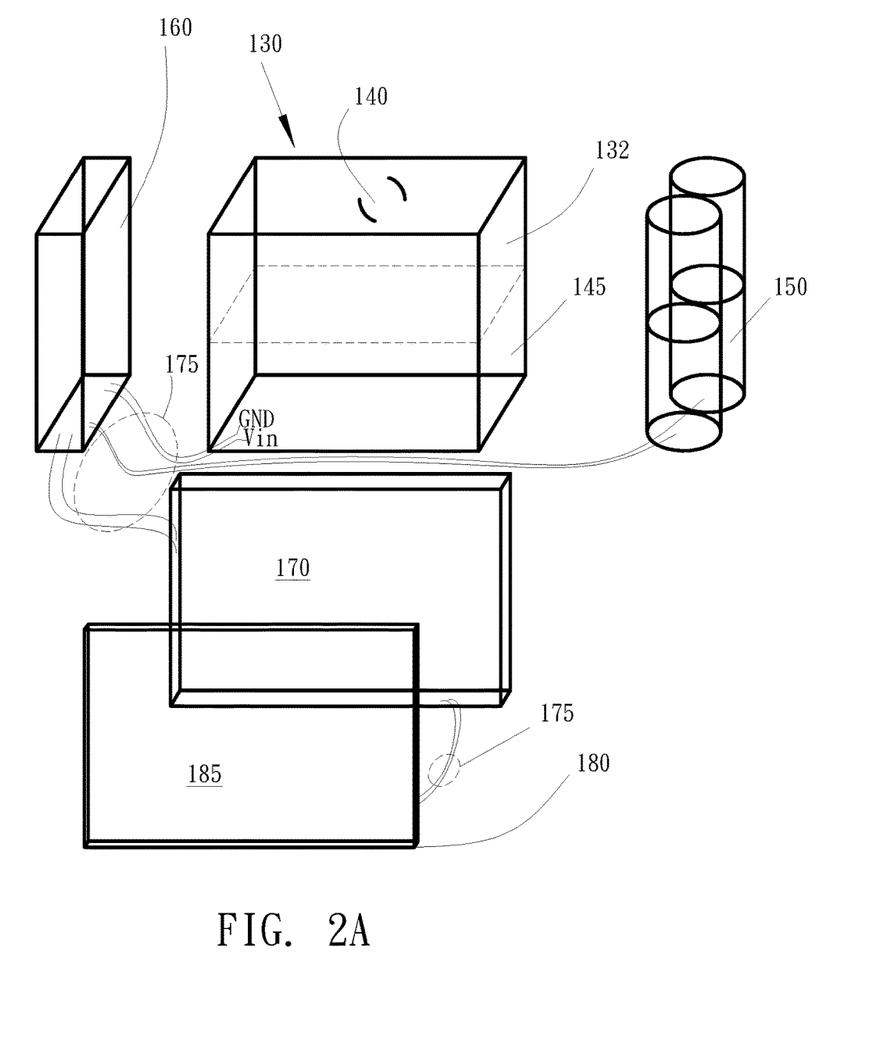
FIG. 2A is a schematic view of the handheld X ray device body internal components in accordance with a preferred embodiment of the present invention.

Referring to FIG. 1 and FIG. 2A, a perspective view of handheld X-ray generator 100 and a schematic view of an internal body 110 of the hand-held X-ray generator, respectively, are shown. In FIG. 1, the handheld X-ray generator body is like a camera. A zoom ring-like object 120 at the front face of the X-ray device body 110 is an X-ray exit. A lead shell 122 is either as a liner inside the zoom ring-like object 120 or as a jacket wrapped the outside surface of the zoom ring-like object 120. A side of the X-ray device body has a buckle 112 provided for a strap there through to relieve the loading of the operator. Inside the X-ray generator body has a rectangular block 130, a battery 150, an oscillation circuit 160 and a control circuit 170. The control circuit 170 including a microprocessor with a LCM driving circuit is connected to a rear panel 180 of the X-ray body 110 as an operator interface. The rear panel 180 includes a LCD panel 185 and a plurality of signal-indicators and a plurality of keys. The numeric 175 represents connecting power cord and/or signal lines to connect foresaid modules.

Figure 2B:
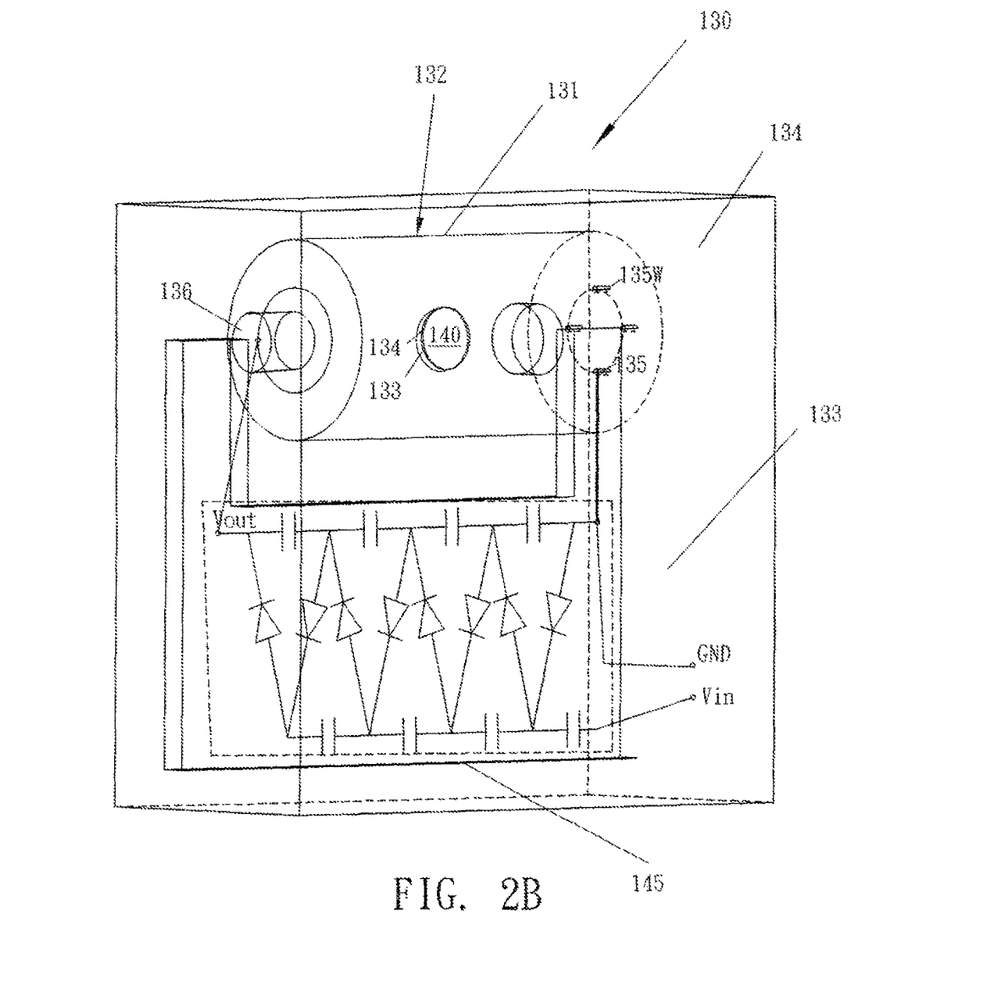
FIG. 2B is a schematic view of the main component of the handheld X ray device showing an encapsulated structure of a glass ball tube and a voltage boosting circuit in accordance with a preferred embodiment of the present invention.
Figure 2C:
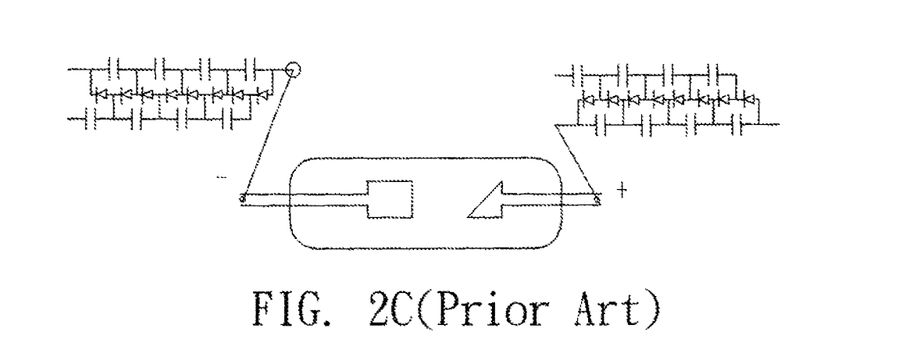
FIG. 2C illustrates a handheld X ray device having two sets of voltage boosting modules, connected to the anode electrode and the cathode electrode, respectively, in accordance with the prior art.
Figure 2D:
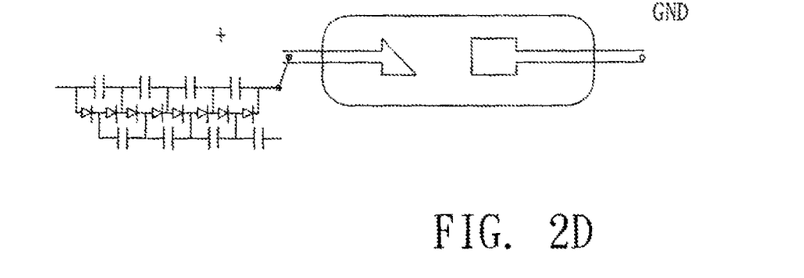
FIG. 2D illustrates a handheld X ray device having one voltage boosting module with high voltage terminal connected to the anode electrode pin in accordance with the present invention.

Referring to FIG. 2B, rectangular block 130 is main portion of the X-ray device body 110 comprises a glass ball-tube 132 and a voltage boosting circuit 145. Both of them are sealed by a layer of insulating gel 133, a high voltage breakdown resisting gel and then wrapped by a lead shell 134. The glass ball-tube 132 has a cathode electrode pin 135 connecting the cold cathode and a wire end of tungsten filament, a single-used pin 135W connecting the other wire end of the tungsten filament, an anode electrode pin 136 connecting the anode target extended out. Furthermore, the cathode electrode pin 135 and the anode electrode pin 136 are respectively, connected to the ground terminal and the high voltage output terminal of the voltage boosting module 145. In accordance with the present invention, one set of the voltage boosting module 145 is enough to reach a determined high voltage 65-70 kV from the ground. By contrast, there are two sets of the voltage boosting module are demanded according to the conventional technology, as shown in FIG. 2C, since boosting to such a high voltage resulted in a very low current. However, a much larger current output is demanded according to prior art comparing to that of the present invention. The two sets of voltage boosting module are provided by a first set of power with voltage −35 k-0V connected to the cathode electrode and a second set of power with voltage 0V-35 kV connected to the anode electrode. One set of the voltage boosting module 145 connected to the anode reduces the volume and the weight, as shown in FIG. 2D. It is easier to be as a handheld X ray device.

As aforementioned the glass ball-tube 135, there are a base a cold cathode, a tungsten filament a focus cap and an anode target. The single use pin 135W is specially utilized in the vacuuming process to shorten the vacuuming time cost and keep the vacuum level for a long time. After an open end of the glass ball-tube is sealed by melting. A Taiwan patent application with Application number No. 103140325 filed on date of Nov. 20, 2014, which is incorporated herein by reference.

Surely, an X-ray window 140 is preserved at the rectangular block 130. The X-ray window 140 is aligned with the zoom ring-like object 120. To prevent any X-rays leakage, the glass ball-tube is wrapped by a first lead shell 131 first except the X-ray window 140, and aforesaid electrode pines 136, 135, 135W. Thereafter, the rectangular block 130 with the insulating gel is wrapped again by a second lead shell 134. The camera-like X-ray device body has a feature of a collimating section 125 at top surface of the zoom ring-like object 120, wherein there is an incline angle $\Theta$ of about 10-30° down based from the upper surface of the X-ray device body, as shown in FIG. 1. The incline angle $\Theta$ of the zoom ring-like object 120 is based on ergonomic calculation so that the operator can collimate the irradiated target easily and safely. The collimating section 125 is composed of a line segment, a ledge, or a small groove, or a front sight blade, at the top surface of zoom ring-like object 120 to provide the operator collimating the irradiated target easily.

The handheld X-ray generator 100 is a cold cathode type without cooling water during operation and a current is of about 100-200 µA. It can be used continuously. By contrast, the conventional X-ray generator, tungsten filament type, needs cooling water. The known hand-hand X-ray device, Nomad pro 2 made by ARIBEX company has duty-cycle limitation during operation. In each shot, it has to rest for at least one minute air cooling.

Figure 3:
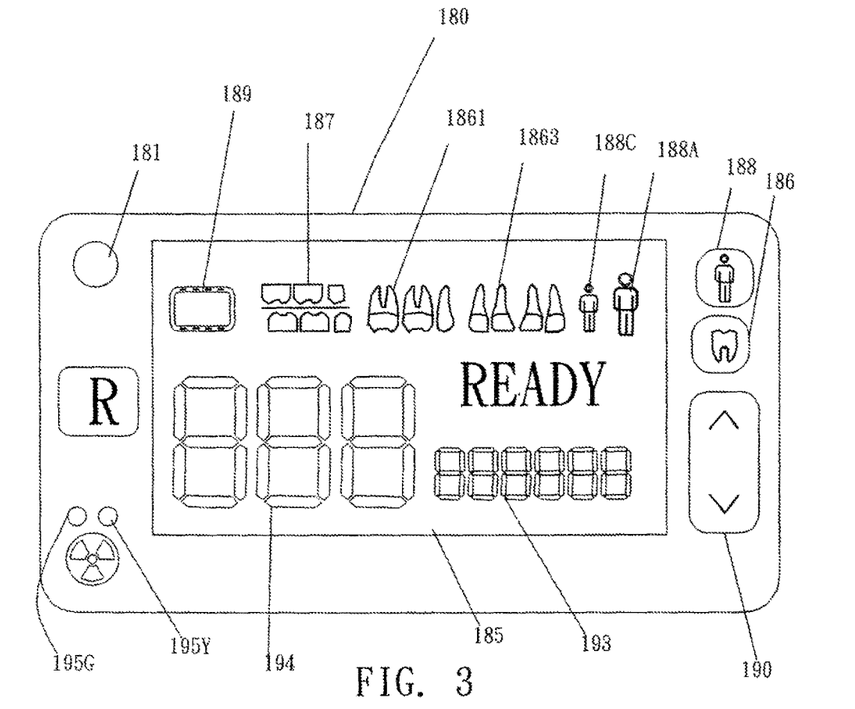
FIG. 3 illustrates rear panel of the handheld X ray device showing a LCD display as a user interface in accordance with the present invention.

Please refer to FIG. 1 and FIG. 3, the X-ray device body 110 has a trigger 117 at the top surface. The rear panel 180 is a user interface 180 and a power button 181. After the button 181 is pressed to start, the LCD panel 185 is turned on. As shown in the schematic of FIG. 3, the display, illustrates of a molar icon 1861, a canine teeth icon 1863, a tooth occlusion status icon 187, an adult icon 188A or a child icon 188C. Each of them is set to have different default dose (irradiation seconds). An operator could press entity key 186 moving cursor to select the type of tooth icons among the molar icon 1861, the canine teeth icon 1863, and the tooth occlusion status icon 187 and press entity key 188 moving cursor to select the adult icon 188A or the child icon 188C. After setting, the 7-segment LED 194 displays a default irradiation time. If necessary, the operator could adjust the default dose by pressing the upper key or down key 190 in accordance with the situation of the patient's condition. Thereafter, the operator utilizes the collimator section 125 to carry out the irradiation target alignment. The 7-segment LED 194 is provided to count the total shot numbers relating to maintain warranty available when maintenance personnel access to the interior setting by reference. It shows "SEC" only in the usually time.

The handheld X-ray generator 100 hasn't a viewfinder according to the present invention. The collimator section 125 could assist the operator precisely alignment. Even though the preparatory work is finished, the X ray trigger 117 doesn't not actuation still until a security button R is pressed and a green indicator 195G is lighted on. The green indicator 195G lighted on is used to indicate the X-ray generator in a ready status. Thus the security key R is a ready key. After the X-ray generator is in a ready status, the electricity power of the battery is boosted up the low voltage of the battery carried to a target voltage by the oscillation circuit 160 associated with the voltage boosting module 145. When the X Ray generator is ready, the X ray trigger 117 can be actuated and while the green indicator 195G is lighted off, the yellow indicator 195 lighting on is followed. After the yellow indicator 195Y is lighted off again, it represents the X ray irradiation action is finished.

Alternatively, the LCD panel may include a touch panel so that the keys 186, 188 are soft keys instead.

The benefits of the present invention are:

(1). the handheld X-ray generator can be shot continuously and with very good penetration under a voltage of about 65 kV. In comparison with the conventional handheld X-ray device, the latter needs air cooling after each shot, thus, at least 1 minute rest for each shot is necessary.

(2) the vacuum level in the glass ball-tube can be kept well so that the X-ray photo quality is the same as the initial even after several thousand shots. The X-ray photo quality is found that becomes worse after 100 shots if the handheld X-ray generator without a tungsten filament inside to assist vacuuming the glass ball-tube.

(3) in comparing with the Normad pro 2, the dosage of the X-ray according to the present invention is very low but the X-ray photo quality is still kept well. The X-ray generator gives least damage while using for human chest, dental care, and skeletal irradiation and is thus better than the conventional, which demands high dosage.

(4) both of the glass ball tube and the voltage booting module are encapsulated by an insulating gel and is then wrapped by lead shell thus, it could prevent the handheld X-ray generator from corona discharge during high voltage operation and X ray leakage.

(5) the X ray window is aligned with the zoom ring-like object 120. The zoom ring-like object 120 has a lead shell either as a liner or as a wrapper to prevent X rays from leakage. Besides, with the collimator 125 at the top of the zoom ring-like object 120, the operator can do the alignment easier.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structures.

What is claimed is:

1. A handheld X ray device comprising:
   a camera-like X ray generator body having a zoom ring-like object at a front side of said X ray generator body as an exit of X rays;
   inside said camera-like X ray generator body, having a glass ball-tube and only one voltage boosting circuit encapsulated by an insulating gel and wrapped by a lead shell except for an X ray window, wherein said voltage boosting circuit is provided to output a predetermined high voltage to an anode electrode pin, and a ground terminal connected to a cold cathode pin, said anode electrode pin and said cold cathode pin are extended out from the glass ball-tube, and said glass ball-tube is a cold cathode type X-ray generator with a tungsten filament at a periphery of a cold cathode; and
   an oscillator circuit, a battery, and a control circuit, said battery providing electrical power of said handheld X ray device, and said oscillator circuit and said voltage boosting circuit boosting a voltage up to 40 kV~70 kV from a voltage of said battery under control by said control circuit; and
   a user interface connected to said control circuit installed at a rear surface of said X ray generator body so that an operator can set or change a default value according to conditions of a patient, and said user interface having a security button to prevent said handheld X ray device from being actuated unsafely;
   wherein said zoom ring-like object has an incline angle of about 15-60° downward based on a top plane of said camera-like X ray generator body and a collimator section atop a surface of said zoom ring-like object provided for performing alignment.

2. The handheld X ray device according to claim 1 wherein said user interface comprises a plurality of entity keys and signal indicators and a liquid crystal display, connected with said control circuit to choose an appropriate irradiation time according to conditions of a patient to be X ray irradiated.

3. The handheld X ray device according to claim 2 wherein signal indicators are to express status of said handheld X ray device in a ready status or in a finished status.

* * * * *